United States Patent
Okada et al.

(10) Patent No.: US 12,193,875 B2
(45) Date of Patent: Jan. 14, 2025

(54) ULTRASOUND DIAGNOSTIC APPARATUS AND STORAGE MEDIUM

(71) Applicant: KONICA MINOLTA, INC., Tokyo (JP)

(72) Inventors: Kaoru Okada, Hino (JP); Yuichi Nishikubo, Kawasaki (JP); Hiroaki Kikuchi, Kawaguchi (JP)

(73) Assignee: KONICA MINOLTA, INC., Tokyo (JP)

( * ) Notice: Subject to any disclaimer, the term of this patent is extended or adjusted under 35 U.S.C. 154(b) by 48 days.

(21) Appl. No.: 17/831,655

(22) Filed: Jun. 3, 2022

(65) Prior Publication Data

US 2023/0024782 A1 Jan. 26, 2023

(30) Foreign Application Priority Data

Jul. 15, 2021 (JP) .................................. 2021-116805

(51) Int. Cl.
*A61B 8/00* (2006.01)
*A61B 5/00* (2006.01)

(52) U.S. Cl.
CPC .......... *A61B 8/4444* (2013.01); *A61B 5/6843* (2013.01); *A61B 8/4227* (2013.01); *A61B 8/4245* (2013.01); *A61B 2562/0247* (2013.01)

(58) Field of Classification Search
CPC .......... A61B 2562/0247; A61B 5/6831; A61B 5/684; A61B 5/6843; A61B 5/6844;
(Continued)

(56) References Cited

U.S. PATENT DOCUMENTS

2007/0032726 A1* 2/2007 Osaka ...................... A61B 8/08
600/459
2011/0040187 A1* 2/2011 Matsumura .......... A61B 5/6843
600/443
(Continued)

FOREIGN PATENT DOCUMENTS

JP        H07051264 A    2/1995
KR   20070109293 A * 11/2007

OTHER PUBLICATIONS

Translated Hyun KR 20070109293 (Year: 2007).*

*Primary Examiner* — Joseph M Santos Rodriguez
*Assistant Examiner* — Brooke Lyn Klein
(74) *Attorney, Agent, or Firm* — Holtz, Holtz & Volek PC

(57) ABSTRACT

An ultrasound diagnostic apparatus includes: an image generator that generates ultrasound image data based on a reception signal received from an ultrasound probe that sends and receives ultrasound waves; a fastener that attaches the ultrasound probe to a subject and fastens the ultrasound probe on the subject such that a pressure applied to the subject to which the ultrasound probe is attached is adjustable; and a hardware processor. The hardware processor controls driving of the fastener, based on difference information between before fastening the ultrasound probe and during/after fastening the ultrasound probe, the difference information being on at least one of positional information on a position of an observation target of the subject, angle information on an angle of the observation target, and pressure information on a pressure applied to the subject.

7 Claims, 11 Drawing Sheets

(58) Field of Classification Search
CPC ....... A61B 8/08; A61B 8/4227; A61B 8/4444; A61B 8/461; A61B 8/485; A61B 8/5246
See application file for complete search history.

(56) References Cited

U.S. PATENT DOCUMENTS

2012/0083692 A1* 4/2012 Stoll ................. A61B 8/429
　　　　　　　　　　　　　　　　　　　　600/437
2022/0361844 A1* 11/2022 Shoudy ................. A61N 7/02

* cited by examiner

ULTRASOUND DIAGNOSTIC APPARATUS AND STORAGE MEDIUM

CROSS-REFERENCE TO RELATED APPLICATIONS

The entire disclosure of Japanese Patent Application No. 2021-116805 filed on Jul. 15, 2021 is incorporated herein by reference in its entirety

BACKGROUND

The present disclosure relates to an ultrasound diagnostic apparatus and a storage medium.

TECHNOLOGICAL FIELD

A widely known ultrasound diagnostic apparatus emits ultrasound waves with an ultrasound probe to the interior of a subject, receives the reflected waves, and analyzes the reflected waves to examine the interior of the subject. Such an ultrasound diagnostic apparatus enables nondestructive and noninvasive examinations of a subject and is widely used in various fields, such as medical examinations and examinations of the interior of buildings/structures.

The ultrasound probe of the ultrasound diagnostic apparatus may be fastened on the subject (e.g., a patient who is walking) with a band to scan the interior of the subject's living body. When the band is wound around the subject, the ultrasound probe may be shifted in the band-pulling direction or may be fastened too tightly. To avoid such issues, the ultrasound probe is fastened on the subject in the following steps of (1) to (5).

(1) An operator (e.g., doctor) manually positions the ultrasound probe to the affected part of the subject to be observed without using the band while looking at an ultrasound image.
(2) The operator attaches the ultrasound probe to the subject by winding the band.
(3) The operator adjusts the shifted ultrasound probe while looking at the ultrasound image.
(4) The operator again adjusts the strength of winding the band.
(5) The operator repeats the steps (2) to (4).

According to JP H07-51264A, an ultrasound probe apparatus includes an ultrasound probe that is attachable to the subject by changing its shape along the surface of the subject body. The ultrasound probe apparatus further includes a driving unit that slidingly or rotationally changes the ultrasound-wave emission direction of the ultrasound probe to a desired direction after the ultrasound probe is attached to the subject.

SUMMARY

According to the above steps (1) to (5), the operator has to repeat fastening and adjustment manually in order to fasten the ultrasound probe. This may be a burden on the operator. Further, according to the ultrasound probe device disclosed in JP H07-51264A, the operator has to slide or rotate the ultrasound probe manually after the ultrasound probe is attached to the subject. When being unable to obtain desired ultrasound images, the operator has to manually reattach the ultrasound probe. This may be a burden on the operator.

According to the ultrasound probe device disclosed in JP H07-51264A, the operator can adjust the ultrasound-wave emission direction of the ultrasound probe but cannot adjust the positional deviation of the flat surface of the ultrasound probe on the body surface and the pressure unevenness of the ultrasound probe device on the subject. As a result, desired ultrasound image data may not be obtained.

Objects of the present invention include easily and appropriately fastening the ultrasound probe to a subject.

To achieve at least one of e above objects, according to an aspect of the present invention, there is provided an ultrasound diagnostic apparatus including: an image generator that generates ultrasound image data based on a reception signal received from an ultrasound probe, the ultrasound probe sending and receiving ultrasound waves; a fastener that attaches the ultrasound probe to a subject and fastens the ultrasound probe on the subject such that a pressure applied to the subject to which the ultrasound probe is attached is adjustable; and a hardware processor that controls driving of the fastener, based on difference information between before fastening the ultrasound probe and during/after fastening the ultrasound probe, the difference information being on at least one of positional information on a position of an observation target of the subject, angle information on an angle of the observation target, and pressure information on a pressure applied to the subject.

According to another aspect of the present invention, there is provided a non-transitory computer-readable storage medium storing a program for a computer of an ultrasound diagnostic apparatus that includes: an image generator that generates ultrasound image data based on a reception signal received from an ultrasound probe that sends and receives ultrasound waves; and a fastener that attaches the ultrasound probe to a subject and fastens the ultrasound probe on the subject such that a pressure applied to the subject to which the ultrasound probe is attached is adjustable, wherein the program causes the computer to function as a hardware processor that controls driving of the fastener, based on difference information between before fastening the ultrasound probe and during/after fastening the ultrasound probe, the difference information being on at least one of positional information on a position of an observation target of the subject, angle information on an angle of the observation target, and pressure information on a pressure applied to the subject.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein.

DETAILED DESCRIPTION OF THE EMBODIMENTS

The first and second embodiments of the present invention are described with reference to the drawings. However, the scope of the present invention is not limited to the disclosed embodiments and drawings.

First Embodiment

Figure 1:
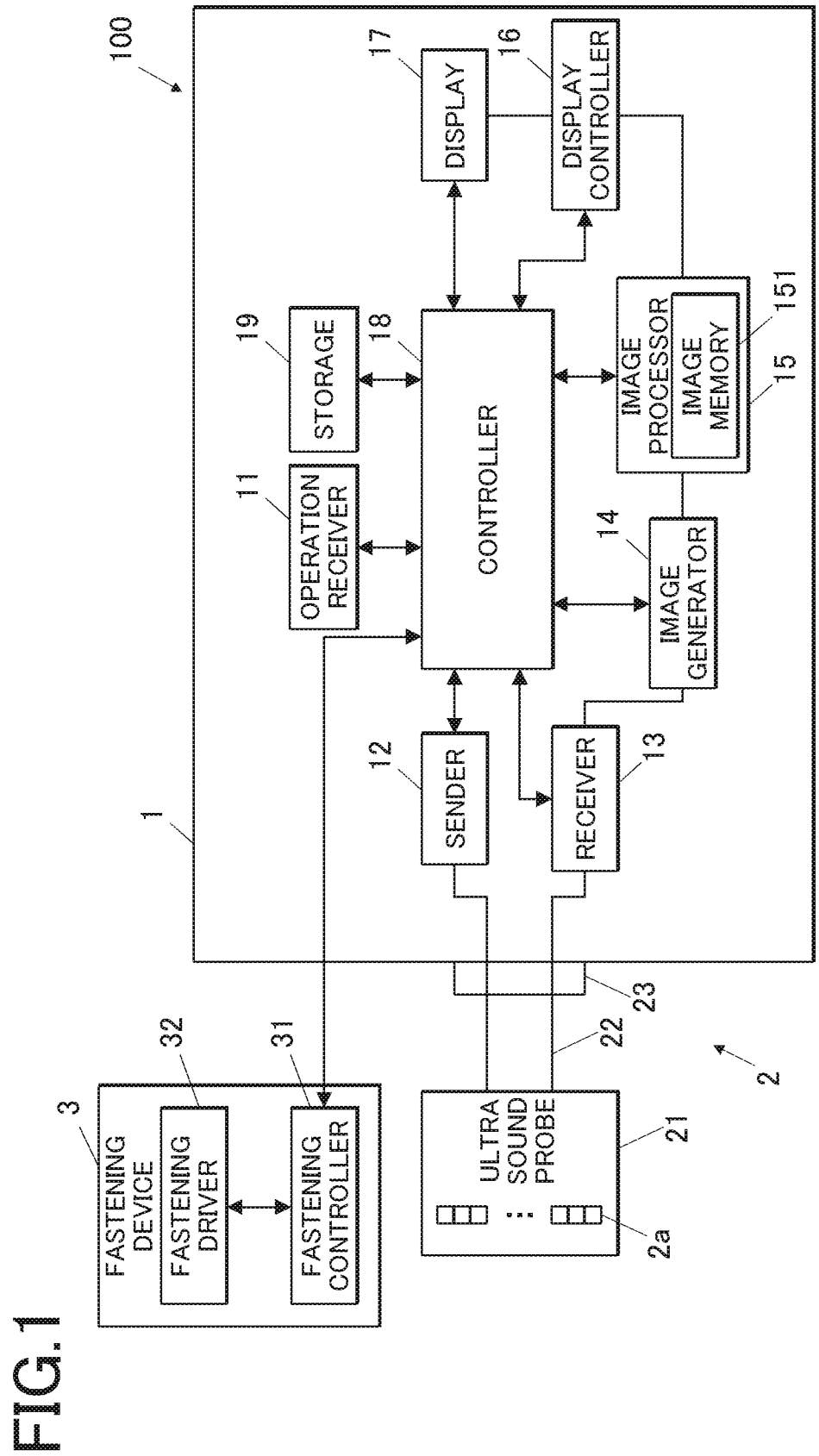
FIG. 1 is a block diagram showing functional components of an ultrasound diagnostic apparatus in a first embodiment of the present invention.

The first embodiment of the present invention is described with reference to FIG. 1 to FIG. 7. Firstly, the entire configuration of an apparatus in this embodiment is described with reference to FIG. 1. FIG. 1 is a block diagram showing functional components of an ultrasound diagnostic apparatus 100 in this embodiment.

As shown in FIG. 1, the ultrasound diagnostic apparatus 100 in this embodiment is movably installed in a consultation/examination room of a medical facility (e.g., hospital). The ultrasound diagnostic apparatus 100 is operated by an operator, such as a doctor or a technical expert.

As shown in FIG. 1, the ultrasound diagnostic apparatus 100 includes an ultrasound diagnostic apparatus main body 1, an ultrasound probe 2, and a fastening device 3 as a fastener. The ultrasound diagnostic apparatus main body 1 is connected to the ultrasound probe 2. The ultrasound probe 2 sends ultrasound waves (sending-ultrasound waves) into the subject (e.g., the living body of the patient) and receives reflected waves that are reflected in the subject (reflected ultrasound waves: echoes). The ultrasound probe 2 includes an ultrasound probe main body 21, a cable 22, and a connector 23. The ultrasound probe main body 21 is the head part of the ultrasound probe 2 that sends and receives ultrasound waves. The cable 22 connects the ultrasound probe main body 21 and the connector 23 and flows driving signals for the ultrasound probe main body 21 and receipt signals, which are ultrasound waves. The connector 23 is a plug connector to be connected to a not-illustrated receptacle connector of the ultrasound diagnostic apparatus main body 1.

The ultrasound diagnostic apparatus main body 1 is connected to the ultrasound probe main body 21 via the connector 23 and the cable 22. The ultrasound diagnostic apparatus main body 1 sends electric driving signals to the ultrasound probe main body 21 to cause the ultrasound probe main body 21 to send sending ultrasound waves toward the subject. When the ultrasound probe main body 21 receives reflected ultrasound waves from inside the subject, the ultrasound probe 2 generates electric reception signals. On the basis of the generated reception signals, the ultrasound diagnostic apparatus main body 1 generates ultrasound image data, thereby imaging the internal condition of the subject.

The ultrasound probe main body 21 includes transducers 2a at the leading end side. The transducers 2a are piezoelectric elements that send and receive ultrasound waves. The transducers 2a are arranged in a one-dimensional array in the azimuth direction (scanning direction), for example. The number of transducers 2a may be determined as desired. This embodiment uses a linear-scanning electronic scan probe as the ultrasound probe 2. However, the ultrasound probe may be an electronic scan type or a mechanical scanning type. Further, the ultrasound probe may be a linear scanning type, sector scanning type, or convex scanning type. The ultrasound diagnostic apparatus main body 1 may wirelessly communicate with the ultrasound probe 2 (ultrasound probe main body 21) over an ultra wide band (UWB), instead of communicating via the wire 22.

The ultrasound probe 2 in this embodiment is formed to be attachable to the subject (e.g., living body of the patient) when in use. For example, the ultrasound probe 2 is used by being fastened with the fastening device 3 to the leg of a patient who is walking Herein, for example, the direction in which the ultrasound probe main body 21 sends/receives ultrasound waves is orthogonal to the direction in which the cable 22 of the ultrasound probe main body 21 is connected. The direction in which the ultrasound probe main body 21 sends/receives ultrasound waves may not be orthogonal to the direction in which the cable 22 of the ultrasound probe main body 21 is connected.

The fastening device 3 is for fastening the ultrasound probe 2 to the subject. The fastening device 3 includes a fastening controller 31 and a fastening driver 32 as well as the fastening member. The fastening controller 31 is connected to the ultrasound diagnostic apparatus main body 1 and controls the fastening driver 32 under the control of a controller 18, which is descried later. The fastening driver 32 electrically drives the fastening member (e.g., by a motor). The fastening driver 32 is driven to wind (tighten) the band (fastening member) around the subject under the control of the fastening controller 31, thereby fastening the ultrasound probe 2 to the subject. Specific examples of the fastening device 3 are described later.

The ultrasound diagnostic apparatus main body 1 includes an operation receiver 11, a sender 12, a receiver 13, an image generator 14, an image processor 15, a display controller 16, a display 17, a controller 18 (hardware processor), and a storage 19, for example.

The operation receiver 11 includes operation tools, such as a push button(s), an encoder (rotary knob), a lever switch, a joystick, a trackball, a keyboard, a touchscreen, or a multifunctional switch as a combination of the aforementioned operation tools. The operation receiver 11 receives inputs of various operations by the operator via the operation tools and outputs the operation information to the controller 18.

The sender 12 is a circuit that supplies the ultrasound probe 2 with electric driving signals under the control of the controller 18 and causes the ultrasound probe 2 to generate sending ultrasound waves. The sender 12 includes a clock generating circuit, a delay circuit, and a pulse generating circuit, for example. The clock generating circuit generates clock signals that determine timings to send driving signals and sending frequency. The delay circuit sets a delay time for each of individual pathways corresponding to each of the transducers 2a and delays transmission of driving signals by the set delay time. The delay circuit thus converges sending beams consisting of sending ultrasound waves. The pulse generating circuit generates pulse signals (driving signals) at a predetermined cycle. The sender 12 configured as described above drives part of transducers 2a (e.g., 64 transducers 2a) among the transducers 2a arranged in the ultrasound probe 2 (e.g., 192 transducers 2a) to generate sending ultrasound waves, for example. The sender 12 performs a scan by shifting the transducers 2a to be driven in the azimuth direction (scanning direction) each time sending ultrasound waves are generated.

The receiver 13 is a circuit that receives electric reception signals from the ultrasound probe 2 under the control of the controller 18. The receiver 13 includes an amplifier, an analog-to-digital (A/D) converter circuit, and a delay-and-sum circuit, for example. The amplifier is a circuit that amplifies reception signals at a predetermined amplification factor with respect to each of individual pathways corresponding to the respective transducers 2a. The A/D converter circuit converts the amplified reception signals by A/D conversion. The delay-and-sum circuit aligns the time phase of the A/D converted reception signals by adding a delay time with respect to each of the individual pathways corresponding to the respective transducers 2a and sums (delays and sums) the aligned reception signals to generate sound ray data.

Under the control of the controller 18, the ge generator 14 performs envelope demodulation and logarithmic compression on the sound ray data input from the receiver 13 and further adjusts the dynamic range and the gain. Thus, by conversion to brightness, the image generator 15 generates a B-mode (brightness-mode) image data that consists of pixels having brightness values as received energy. That is, the B-mode image data represents the intensity of the reception signals by brightness. In addition to the B-mode image data as ultrasound image data of B imaging mode, the image generator 14 may be able to generate ultrasound image data of other imaging modes, such as A (Amplitude) mode, M (Motion) mode, image modes based on a Doppler method (e.g., color Doppler mode).

Under the control of the controller 18, the image processor 15 performs image processing on the B-mode image data output from the image generator 14 according to various image parameters having been set. The image processor 15 includes an image memory 151 consisting of a semiconductor memory, such as a dynamic random access memory (DRAM). Under the control of the controller 18, the image processor 15 stores the B-mode image data on which image processing has been performed in the image memory 151 on a frame basis. The image data on a frame basis may be called ultrasound image data or frame image data. Under the control of the controller 18, the image processor 15 sequentially outputs the image data, which are generated as described above, to the display controller 16.

Under the control of the controller 18, the display controller 16 converts the image data received from the image processor 15 into image signals for display and outputs the image signals to the display 17.

The display 17 includes a display panel, such as a liquid crystal display (LCD), an organic electro-luminescence (EL) display, or an inorganic EL display. The display 17 displays various kinds of information on the display screen of the display panel. Under the control of the controller 18 and in accordance with the image signals output from the display controller 16, the display 17 displays the ultrasound image and various kinds of information on the display screen of the display panel.

The controller 18 includes a central processing unit (CPU), a read only memory (ROM), and a random access memory (RAM), for example. The controller 18 reads various processing programs, such as a system program stored in the ROM, loads the programs into the RAM, and controls the operation of each unit of the ultrasound diagnostic apparatus 100 according to the loaded program. The ROM consists of a non-volatile memory (e.g., semiconductor) or the like. The ROM stores the system program for the ultrasound diagnostic apparatus 100, various processing programs executable on the system program, and various kinds of data (e.g., a gamma table). These programs are stored in the form of computer-readable program codes, and the CPU sequentially executes operations in accordance with the program codes. The ROM stores a first fastening adjustment program for executing a first fastening adjustment process, which is described later. The RAM provides a working area for temporarily storing various programs to be executed by the CPU and data relating to the programs.

The storage 19 is a hard disk drive (HDD), a solid state drive (SDD), or the like that readably and writably stores information, such as ultrasound image data.

Part or all of functions of the functional blocks of the components constituting the ultrasound diagnostic apparatus 100 can be achieved by a hardware circuit, such as an integrated circuit. The integrated circuit is a large scale integration (LSI), for example. Depending on the degree of integration, an LSI may also be called an IC (integrated circuit), a system LSI, a super LSI, or an ultra LSI. The integrated circuit may be achieved not by an LSI but by a dedicated circuit or a general-purpose processor. A field programmable gate array (FPGA) or a reconfigurable processor that is reconfigurable in terms of connections and settings of circuit cells in an LSI may also be used. Alternatively, the functions of part or all of the functional blocks can be achieved by a software. In this case, the software is stored in at least one storage medium such as a ROM, an optical disk, or a hard disk, and the software is executed by an arithmetic processor.

Figure 2A:
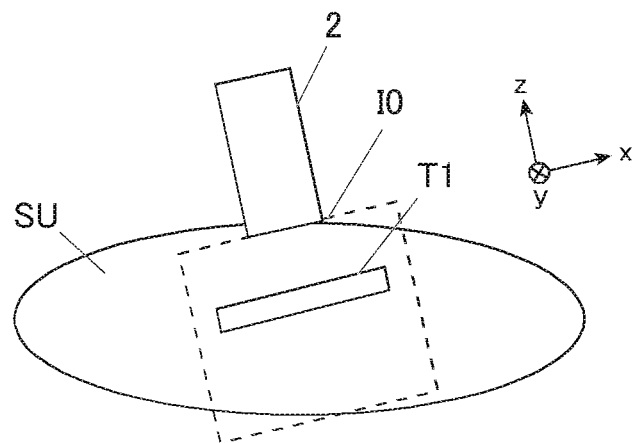
FIG. 2A is a schematic drawing of an ultrasound probe and a subject before the ultrasound probe is fastened.
Figure 2B:
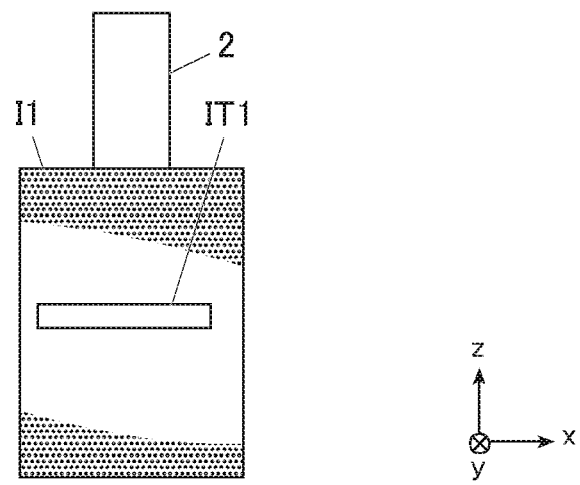
FIG. 2B is a schematic drawing of the ultrasound probe and a B-mode image before the ultrasound probe is fastened.
Figure 2C:
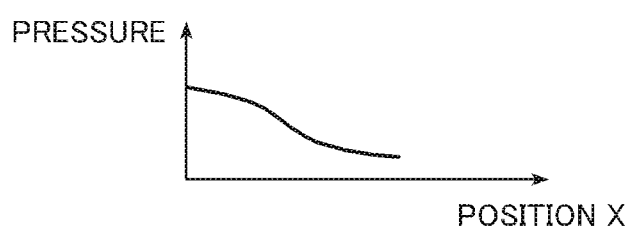
FIG. 2C is a graph of pressure distribution with respect to positions in the scanning direction in the B-mode image before the ultrasound probe is fastened.
Figure 3A:
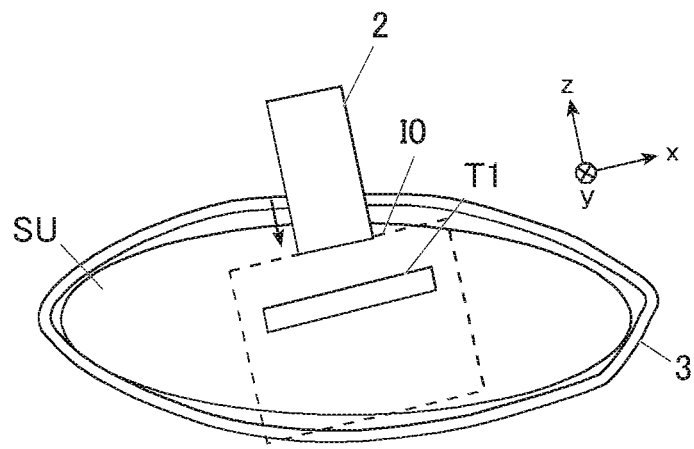
FIG. 3A is a schematic drawing of the ultrasound probe, a fastening device, and the subject after the ultrasound probe is fastened.
Figure 3B:
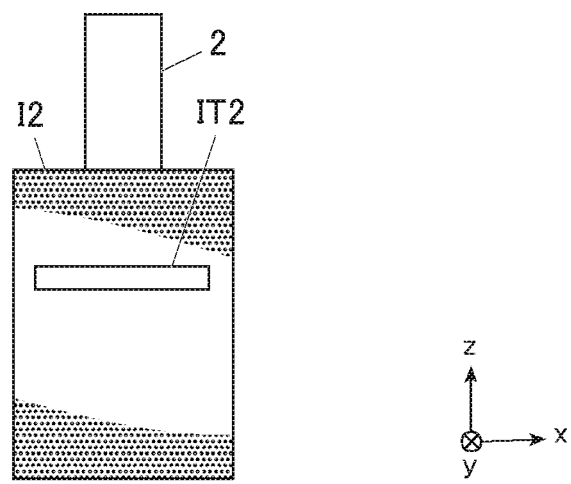
FIG. 3B is a schematic drawing of the ultrasound probe and a B-mode image after the ultrasound probe is fastened.
Figure 3C:
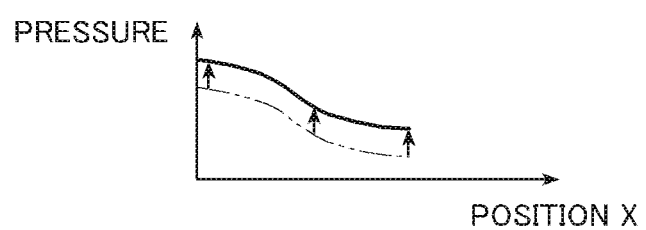
FIG. 3C is a graph of pressure distribution with respect to positions in the scanning direction in the B-mode image after the ultrasound probe is fastened.
Figure 4:
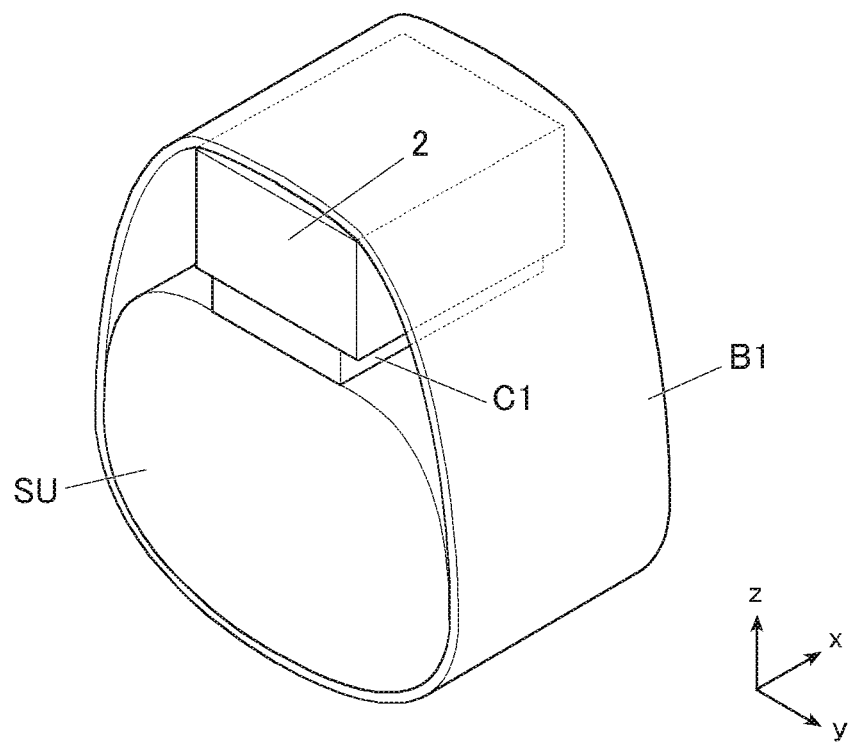
FIG. 4 is a schematic perspective view of the ultrasound probe, a coupler, a band, and the subject in the first embodiment.
Figure 5A:
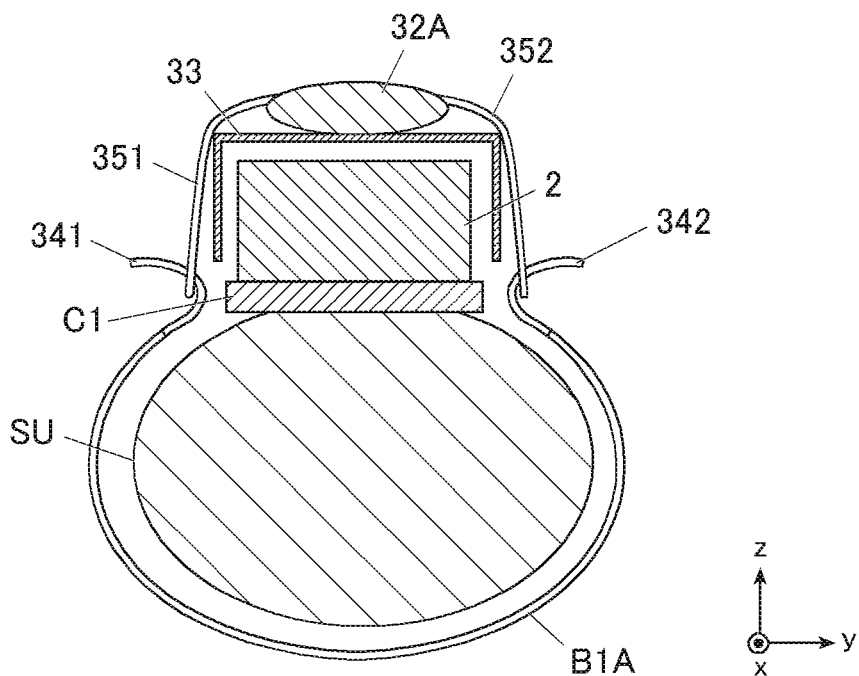
FIG. 5A is a cross section of a first fastening device, the ultrasound probe, and the subject.
Figure 5B:
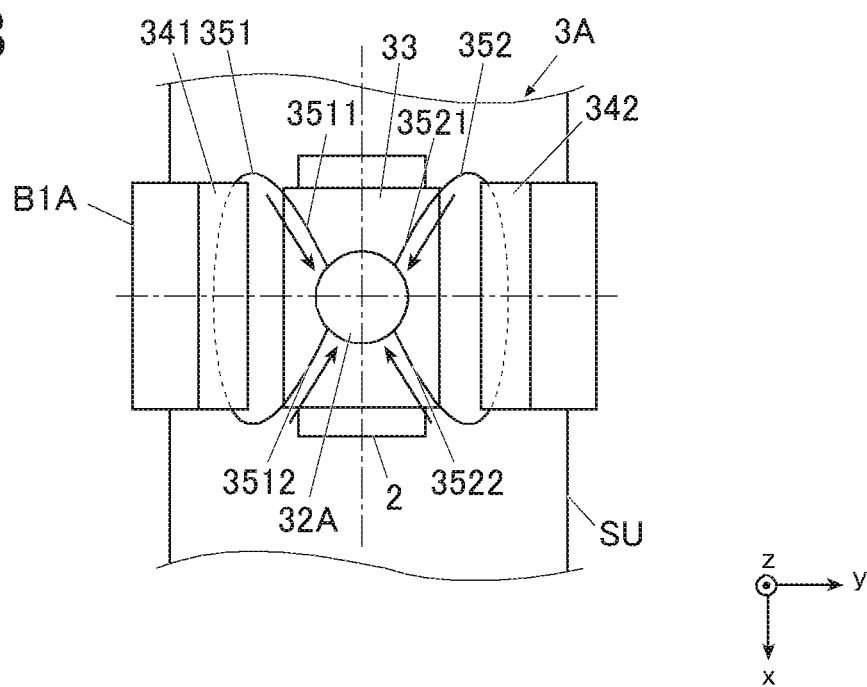
FIG. 5B is a top view of the first fastening device, the ultrasound probe, and the subject.
Figure 6:
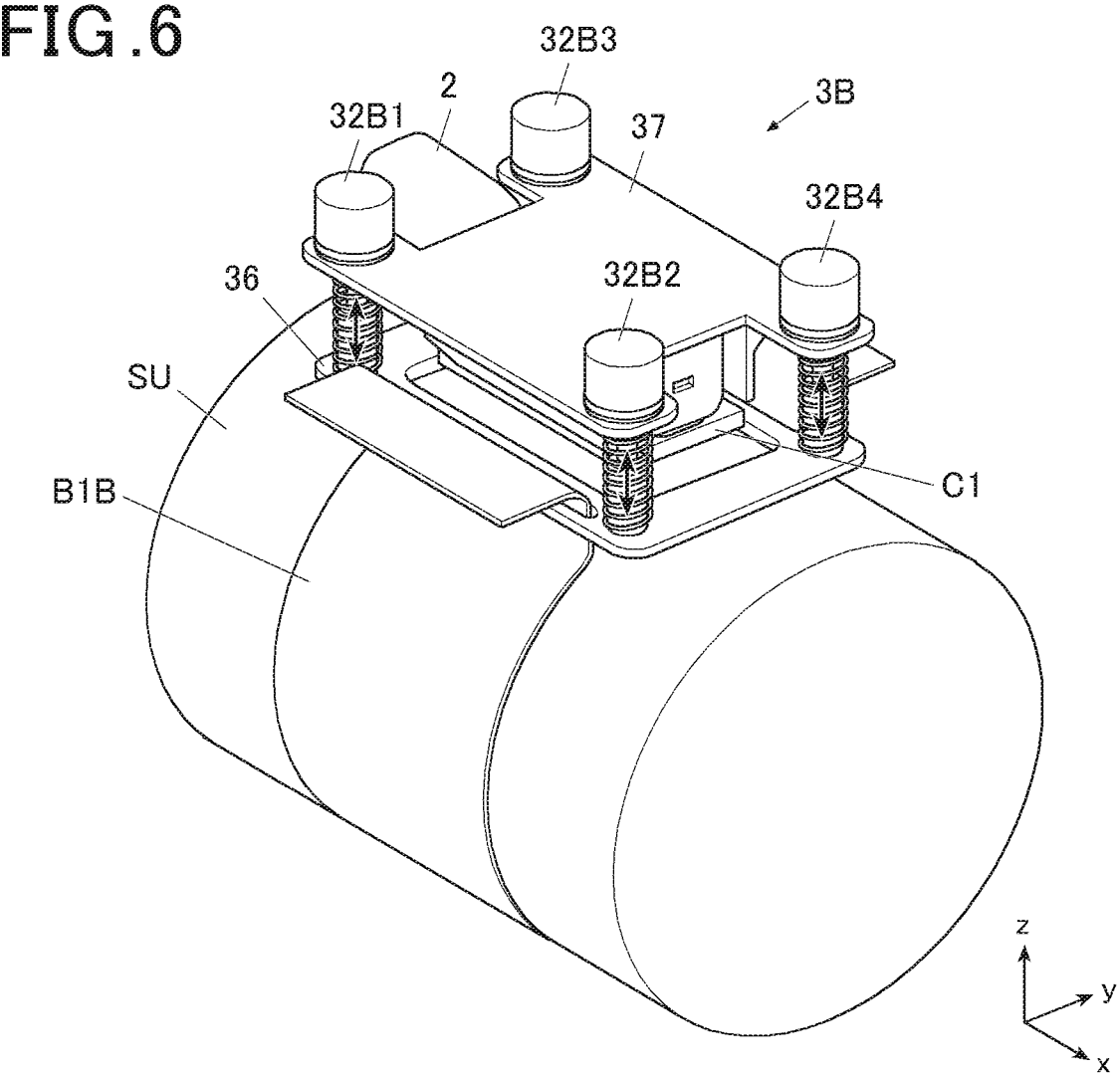
FIG. 6 is a perspective view of a second fastening device, the ultrasound probe, and the subject.

Next, specific examples of the fastening device 3 is described with reference to FIG. 2A to FIG. 6. FIG. 2A is a schematic drawing of the ultrasound probe 2 and the subject SU before the ultrasound probe 2 is fastened. FIG. 2B is a schematic drawing of the ultrasound probe 2 and a B-mode image I1 before the ultrasound probe 2 is fastened. FIG. 2C is a graph of pressure distribution with respect to positions X in the scanning direction in the B-mode image I1 before the ultrasound probe 2 is fastened. FIG. 3A is a schematic drawing of the ultrasound probe 2, the fastening device 3, and the subject SU after the ultrasound probe 2 is fastened. FIG. 3B is a schematic drawing of the ultrasound probe 2 and the B-mode image I2 after the ultrasound probe 2 is fastened. FIG. 3C is a graph of pressure distribution with respect to positions X in the scanning direction in the B-mode image I2 after the ultrasound probe 2 is fastened. FIG. 4 is a schematic perspective view of the ultrasound probe 2, a coupler C1, a band B1, and the subject SU in this embodiment. FIG. 5A is a cross section of the fastening device 3A, the ultrasound probe 2, and the subject SU. FIG. 5B is a top view of the fastening device 3A, the ultrasound probe 2, and the subject SU. FIG. 6 is a perspective view of the fastening device 3B, the ultrasound probe 2, and the subject SU.

An overview of the method to fasten the ultrasound probe 2 with the fastening device 3 according to this embodiment is described with reference to FIG. 2A to FIG. 3C. Described herein is a case where the fastening device 3 fastens the ultrasound probe 2 to the leg of the patient as the subject SU.

As shown in FIG. 2A, before the ultrasound probe 2 is fastened by the fastening device 3, the ultrasound probe 2 is brought into contact with the body surface of the subject SU to observe blood vessels as a target T1. The blood vessels are an example of the observation target in the subject SU. The observation target in the subject SU is not limited to blood vessels. The region I0 is a region to be imaged as a B-mode image by the ultrasound probe 2.

In FIG. 2A, the X, Y, Z axes are defined on the basis of the ultrasound probe 2. The X axis is in the scanning direction in which the transducers 2a are arranged. The Y axis is in an elevation direction orthogonal to the X axis. The Z axis is orthogonal to the X and Y axes. These X, Y, Z axes also apply to other figures.

In the state where the ultrasound probe 2 is not fastened as shown in FIG. 2A, the ultrasound diagnostic apparatus main body 1 generates B-mode image data of the B-mode image I1 as shown in FIG. 2B. The B-mode image I1 includes a target image IT1 of the target T1.

As shown in FIG. 2C, in the B-mode image I1, the distribution of pressures (pressures applied to the subject SU by the ultrasound probe 2) with respect to positions X in the scanning direction may not be equal in the scanning direction (X-axis direction). The pressure distribution indicates the incline of the ultrasound probe 2 in the scanning direction with respect to the subject SU. The pressure distribution on the subject SU may not be equal in the elevation direction as well.

The ultrasound probe 2 is attached and fastened to the subject SU with the band (fastening member of the fastening device 3) as shown in FIG. 3A, and the target T1 (blood vessels as the observation target in the subject SU) is observed with the ultrasound probe 2 in contact with the body surface of the subject SU. Details of the fastening device 3 are omitted in FIG. 3A.

In a state where the ultrasound probe 2 is fastened as shown in FIG. 3A, the ultrasound diagnostic apparatus main body 1 generates B-mode image data of the B-mode image I2 as shown in FIG. 3B. The B-mode image I2 includes a target image IT2 of the target T1.

In FIG. 3C, the solid line represents the pressure distribution (pressure distribution after fastening) in the B-mode image I2 with respect to positions X in the scanning direction (pressure applied to the subject SU by the ultrasound probe 2 and the fastening device 3). The dashed line in FIG. 3C corresponds to the solid line in FIG. 2C, which represents the pressure distribution before the ultrasound probe 2 is fastened. That is, the ultrasound probe 2 is fastened to the subject SU with the fastening device 3 such that the pressure distribution uniformly increases after fastening as compared with before the fastening. FIG. 3 conceptually shows how to wind the band of the fastening device 3, and the specific examples of the fastening device 3 are described later.

Next, the method to detect the pressure applied to the subject in this embodiment is described with reference to FIG. 4. As FIG. 4 conceptually shows, the operator fastens the ultrasound probe 2 and the coupler C1 to the subject SU by using the band B1 of the fastening device 3. Herein, the fastening device 3 includes the coupler C1 as an elastic body. As the band B1 is tightened, the pressure applied to the subject SU increases.

The coupler C1 consists of an elastic body having a predetermined known elastic modulus. The coupler C1 is disposed between the ultrasound sending-receiving surface (the front surface of the ultrasound probe main body 21 of the ultrasound probe 2 in –Z direction) and the body surface of the subject SU. The elastic body of the coupler C1 is made of oil-based gel, such as an oil-phase component containing a macromolecule, for example. The macromolecule constituting the oil-based gel is, for example, a diene macromolecule or a vinyl macromolecule. Specifically, the macromolecule that constitutes the elastic body of the coupler C1 may be natural rubber, isoprene rubber, styrene-butadiene rubber, chloroprene rubber, polyvinyl chloride, polyacrylic acid, polyacrylic ester, or polystyrene. The oil-phase component that contains the macromolecule may be vegetable oil, animal oil, mineral oil, ester oil, or silicon oil, for example. In this embodiment, the macromolecule and the oil-phase component that constitute the oil-based gel are not specified. The elastic body of the coupler C1 may be made of a material other than the oil-based gel. As described above, for the impedance matching between the ultrasound sending-receiving surface of the ultrasound probe 2 and the living body, the elastic body of the coupler C1 may be made of a material with the internal sonic speed of 1470 m/s.

The coupler is primarily used to shift the focal depth of the ultrasound probe. In this embodiment, the coupler C1 is used to estimate (calculate) the pressure at respective positions in the scanning direction (X-axis direction), namely the pressure distribution, on the basis of the predetermined elastic modulus and the change (degree of change) in the length/thickness of the coupler C1 in the depth direction (–Z axis direction) in the B-mode image.

Next, specific examples of the fastening device 3 is described with reference to FIG. 5A to FIG. 6. As a specific example of the fastening device 3, a fastening device 3A is described with reference to FIG. 5A and FIG. 5B.

As shown in FIG. 5A and FIG. 5B, the fastening device 3A includes: a band B1A as a specific example of the band B1; a fastening driver 32A as a specific example of the fastening driver 32; a cover 33 as a fastening member; hook structures 341, 342; wires 351, 352; and the coupler C1.

The band B1A is a belt-shaped band (belt) to be wound around the subject SU. For example, the band B1A is wound around the leg of the patient (living body of the subject SU) such that the belt is wound in a direction of the cross section orthogonal to the direction in which the leg extends (axis direction or X direction in the figures). The cover 33 covers the ultrasound probe main body 21 of the ultrasound probe 2. The scanning direction of the transducers 2a of the ultrasound probe 2 is X-axis direction. The coupler C1 is disposed between the ultrasound sending-receiving surface of the ultrasound probe main body 21 and the subject SU.

The hook structures 341, 342 are fixed to the respective ends of the band B1A. The wires 351, 352 are caught on the respective hook mechanisms 341, 342. The wires 351, 352 are made of metal, for example. The both ends 3511, 3512 of the wire 351 are connected to the fastening driver 32A. The central part of the wire 351 is caught on the hook structure 341, The both ends 3521, 3522 of the wire 352 are connected to the fastening driver 32A. The central part of the wire 352 is caught on the hook structure 342. The wires 351, 352 may be a four-direction belt.

The fastening driver 32A includes a motor, for example. Under the control of the fastening controller 31, the fastening driver 32A winds up or sends out the wires 351, 352. The fastening driver 32A is disposed on the cover 33 at a position corresponding to the center of the arrangement of the transducers 2a of the ultrasound probe 2 in the scanning direction (x-axis direction), for example. The fastening driver 32A can wind up and send out the ends 3511, 3512, 3521, 3522 individually and independently. The ends 3511, 3512, 3521, 3522 are connected to the fastening driver 32A as the center in radial directions at approximately 90-degree intervals. That is, the ends 3511, 3512, 3521, 3522 are connected to the fastening driver 32A in the directions of (x, y)=(−1, −1), (1, −1), (−1, 1), (1,1). By winding up or sending out the wires 351, 352 with the fastening driver 32A, the pressure in −Z direction (direction toward the subject SU) can be adjusted at respective pressure-applied parts in radial directions (parts where the wires 351, 352 are in contact with the cover 33) on the basis of the fastening driver 32A.

Next, a fastening device 3B as a specific example of the fastening device 3 is described with reference to FIG. 6. As shown in FIG. 6, the fastening device 3B includes: a band B1B as a specific example of the band B1; fastening drivers 32B1, 32B2, 32B3, 32B4 as a specific example of the fastening driver 32; a base 36 as a fastening member; a cover 37; and the coupler C1.

The band B1B is a belt-shaped band (belt) to be wound around the subject SU. For example, the band B1B is wound around the leg of the patient (the living body of the subject SU) such that the belt is wound in the direction of the cross section orthogonal to the direction in which the leg extends (axis direction or X direction in the figures). The base 36 is the base of the fastening device 3B. The base 36 is the substantially rectangular bottom plate to be in contact with the body surface of the subject SU. The base 36 has two holes through which the both ends of the band B1B are inserted and one hole through which the ultrasound sending-receiving surface (coupler C1) of the ultrasound probe main body 21 of the ultrasound probe 2 is exposed to the subject SU. The coupler C1 is disposed between the subject SU and the ultrasound sending-receiving surface of the ultrasound probe main body 21.

The cover 37 covers the ultrasound probe main body 21 of the ultrasound probe 2. The cover 37 has a substantially H-shaped flat surface that corresponds to the substantially rectangular base 36. The scanning direction of the transducers 2a of the ultrasound probe 2 is X-axis direction.

The fastening drivers 32B1, 32B2, 32B3, 32B4 each include a motor, a bolt, a nut, and a spring and are disposed at the respective four corners of the flat surface of the base 36 and the cover 37. Specifically, regarding the fastening driver 32B1 as an example, the nut is fixed to the base 36, the motor is fixed to the cover 37, and the rotation shaft of the motor is rotatably connected to the bolt. The bolt is screwed in the nut. The spring is disposed at the external side of the bolt and the nut with the same axis.

For example, when the bolt is tightened by the normal rotation of the motor under the driving control of the fastening controller 31, the distance between the base 36 and the cover 37 (the distance in Z direction) is shortened. Depending on the position of the fastening driver 32B1, the cover 37 presses the ultrasound probe 2 and the coupler C1 in −Z direction, so that the pressure applied to the subject SU increases. Conversely, when the bolt is loosened by the reversal rotation of the motor under the driving control of the fastening controller 31, the distance between the base 36 and the cover 37 is widened. Depending on the position of the fastening driver 32B1, the cover 37 releases the ultrasound probe 2 and the coupler C1 in +Z direction, so that the pressure applied to the subject SU decreases. The structures of the fastening drivers 32B2, 32B3, 32B4 are the same as that of the fastening driver 32B1. The fastening drivers 32B1, 32B2, 32B3, 32B4 can individually and independently apply and release the pressure.

Figure 7:
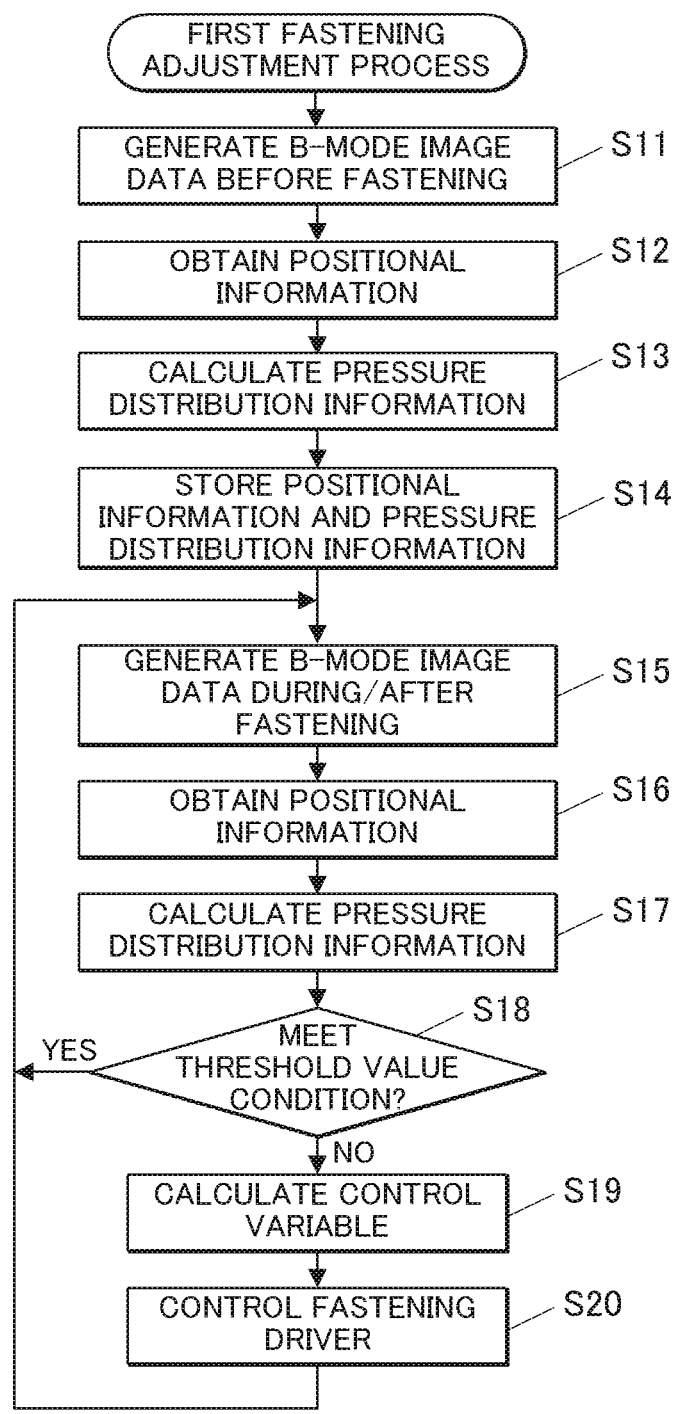
FIG. 7 is a flowchart of a first fastening adjustment process.

Next, operation of the ultrasound diagnostic apparatus 100 is described with reference to FIG. 7. FIG. 7 is a flowchart of a first fastening adjustment process.

The first fastening adjustment process to be performed by the ultrasound diagnostic apparatus 100 is described. The first fastening adjustment process is performed when the ultrasound probe 2 is fastened to the subject to obtain ultrasound image data. In the first fastening adjustment process, the ultrasound probe 2 is automatically fastened to the subject by the fastening device 3 such that the pressure distribution on the subject uniformly increases after fastening the ultrasound probe 2 as compared with the pressure distribution before fastening, on the basis of ultrasound image data before fastening and ultrasound image data during/after fastening (ultrasound image data that is obtained while the ultrasound probe 2 is being fastened or after the ultrasound probe 2 is fastened).

The threshold value condition for difference information is determined beforehand and stored in the storage 19. The difference information indicates the difference between pressure distribution information before fastening and pressure distribution information during/after fastening. The threshold value condition is for determining whether or not to perform automatic fastening control on the basis of the difference information between pressure distribution information before fastening and pressure distribution information during/after fastening. Preferably, the threshold value condition corresponds to (depends on) the region to Which the ultrasound probe 2 is attached.

The operator of the ultrasound diagnostic apparatus 100 attaches the ultrasound probe 2 to an appropriate position of the subject (e.g., leg of a patient) by using the fastening device 3. To allow the operator to check the position of the observation target of the subject, the controller 18 causes the ultrasound probe 2 to send and receive ultrasound waves to generate B-mode image data and displays it on the display 17 in real time by controlling the sender 12, the receiver 13, the image generator 14, the image processor 15, and the display controller 16. The controller 18 keeps the real-time display while performing the first fastening adjustment process.

For example, in response to the operator inputting a command to perform the first fastening adjustment process with the operation receiver 11, the controller 18 of the ultrasound diagnostic apparatus 100 performs the first fastening adjustment process in accordance with the first fastening adjustment program stored in the ROM.

As shown in FIG. 7, the controller 18 firstly generates B-mode image data as ultrasound image data before fastening by controlling the sender 12, the receiver 13, the image generator 14, and the image processor 15 (Step S11). In Step S11, the operator manually adjusts the ultrasound probe 2 and the coupler C1 to achieve appropriate positional information of the observation target and appropriate pressure distribution on the body surface of the subject in order to observe the observation target (e.g., blood vessels or tissues of the subject). The B-mode image data obtained through scanning of the ultrasound diagnostic apparatus 100 in this step is called B-mode image data before fastening. The positional information of the target indicates distribution of positions of the target in the depth direction with respect to positions in the scanning direction on the body surface of the subject. That is, the positional information of the target indicates two-dimensional positional distribution of the target with respect to the body surface.

From the B-mode image of the B-mode image data before fastening generated in Step S11, the controller 18 obtains positional information of the target and the coupler C1 before fastening (Step S12). In Step S12, the controller 18 automatically extracts the target in the B-mode image. For the extraction, the target may be manually specified by the operator through the operation receiver 11 or may be extracted on the basis of extraction condition information. The extraction condition information may be set in Step S12 or may be set by the operator and stored in the storage 19 beforehand, for example. The positional information of the coupler C1 indicates distribution of positions (thickness) in the depth direction with respect to multiple positions in the scanning direction in the B-mode image.

On the basis of the positional information (thickness) of the coupler C1 obtained in Step S12, the controller 18 calculates pressure distribution information before fastening (Step S13). The pressure distribution information before fastening indicates the distribution of pressures on the subject in the scanning direction before the ultrasound probe 2 is fastened. The dimension and the elastic modulus of the coupler C1 are measured beforehand and input by the operator via the operation receiver 11. In Step S13, the controller 18 calculates the pressure distribution information on the subject before fastening on the basis of the dimension and elastic modulus of the coupler C1 and the positional information (thickness) of the deformed coupler C1 obtained in Step S12.

The controller 18 stores, in the storage 19, the positional information of the target before fastening obtained in Step S12 and the pressure distribution information on the subject before fastening obtained in Step S13 (Step S14). After Step S14, the operator may not touch the ultrasound probe 2 attached to the subject and the fastening device 3.

The controller 18 generates B-mode image data during/after fastening by controlling the sender 12, the receiver 13, the image generator 14, and the image processor 15 (Step S15). The B-mode image data during/after fastening may be continuously obtained while the ultrasound probe 2 is being fastened or after the ultrasound probe 2 is once fastened. On the basis of the B-mode image of the B-mode image data during/after fastening generated in Step S15, the controller 18 obtains positional information of the target and the coupler C1 (Step S16). On the basis of the positional information (thickness) of the coupler C1 obtained in Step S16, the controller 18 calculates pressure distribution information during/after fastening (Step S17). The pressure distribution information during/after fastening indicates the distribution of pressures in the scanning direction applied to the subject.

The controller 18 then reads the positional information of the target before fastening, the pressure distribution information on the subject before fastening, and the threshold value condition from the storage 19; calculates difference information between the pressure distribution information before fastening and the pressure distribution information during/after fastening calculated in Step S17; and determines whether the difference information of the pressure distribution information meets the threshold value condition (Step S18). The threshold value condition is that the pressure distribution information during/after fastening is uniformly greater than the pressure distribution information before fastening by a predetermined value (by x Pascal), for example. When the difference information meets the threshold value condition (Step S18: YES), the process proceeds to Step S15.

When the difference information does not meet the threshold value condition (Step S18: NO), the controller 18 calculates the control variable of the fastening driver 32 on the basis of: the positional information of the target before fastening and the pressure distribution information on the subject before fastening that are retrieved in Step S18; the positional information of the target during/after fastening that is obtained in Step S16; and the pressure distribution information on the subject during/after fastening that is calculated in Step S17 (Step S19). The control variable is calculated such that the target remains in the B-mode image even when the subject walks or moves in other ways (e.g., such that the target does not get out of the region of interest (ROI) in the B-mode image, the ROI having been input by the operator via the operation receiver 11) and such that the pressure distribution information uniformly increases along the scanning direction during/after fastening as compared with before fastening (i.e., pressure is uniformly applied in the depth direction). In Step S19, the target that should be kept in the B-mode image may be different from the target to be observed in diagnosis.

On the basis of the control variable for the fastening driver 32, which has been calculated in Step S19, the controller 18 controls the fastening driver 32 via the fastening controller 31 (Step S20) and proceeds to Step S15.

As described above, according to this embodiment, the ultrasound diagnostic apparatus 100 includes: the image generator 14 that generates ultrasound image data based on a reception signal received from the ultrasound probe 2 that sends and receives ultrasound waves; the fastening device 3 that attaches the ultrasound probe 2 to the subject and fastens the ultrasound probe 2 on the subject such that a pressure applied to the subject on which the ultrasound probe 2 is fastened is adjustable; and the controller 18 that controls driving of the fastening device 3, based on difference information between the pressure distribution information on the subject before fastening the ultrasound probe 2 and the pressure distribution information on the subject during or after fastening the ultrasound probe 2. The controller 18 controls driving of the fastening device 3 such that the pressure distribution on the subject before fastening uniformly changes to the pressure distribution on the subject during or after fastening.

According to such a configuration, the ultrasound probe 2 can be fastened on the subject appropriately, automatically, and easily, without causing positional deviation of the ultrasound probe 2 and pressure unevenness on the body surface of the subject. This reduces burdens on the operator and yields desired ultrasound image data.

Preferably, the fastening device 3 may include the coupler C1 that is disposed between the ultrasound probe 2 and the subject and that has a known predetermined elastic modulus. On the basis of the image of the coupler C1 in the ultrasound image of the generated ultrasound image data, the controller 18 calculates pressure distribution information on the subject. Thus, the controller 18 can easily obtain accurate pressure distribution information on the subject.

Preferably, based on threshold value condition concerning whether or not to control the fastening device 3, the controller 18 determines whether the difference information between the pressure distribution information before fastening the ultrasound probe 2 and the pressure distribution information during/after fastening the ultrasound probe 2 meets the threshold value condition. On the basis of the determination, the controller 18 may control driving of the fastening device 3. According to the above feature, the controller 18 can control the driving of the fastening device 3 when the difference information on the pressure distribution information does not meet the threshold value condition. Accordingly, the controller 18 can appropriately control the fastening device 3 when the difference information of the pressure distribution information on the subject does not meet the threshold value condition. Further, control processing load can be reduced.

Preferably, the threshold value condition may correspond to the region of the subject to which the ultrasound probe 2 is attached. This allows the controller 18 to more appropriately control the driving of the fastening device 3, on the basis of the threshold value condition that corresponds to the region of the subject to which the ultrasound probe 2 is attached.

Second Embodiment

Figure 8:
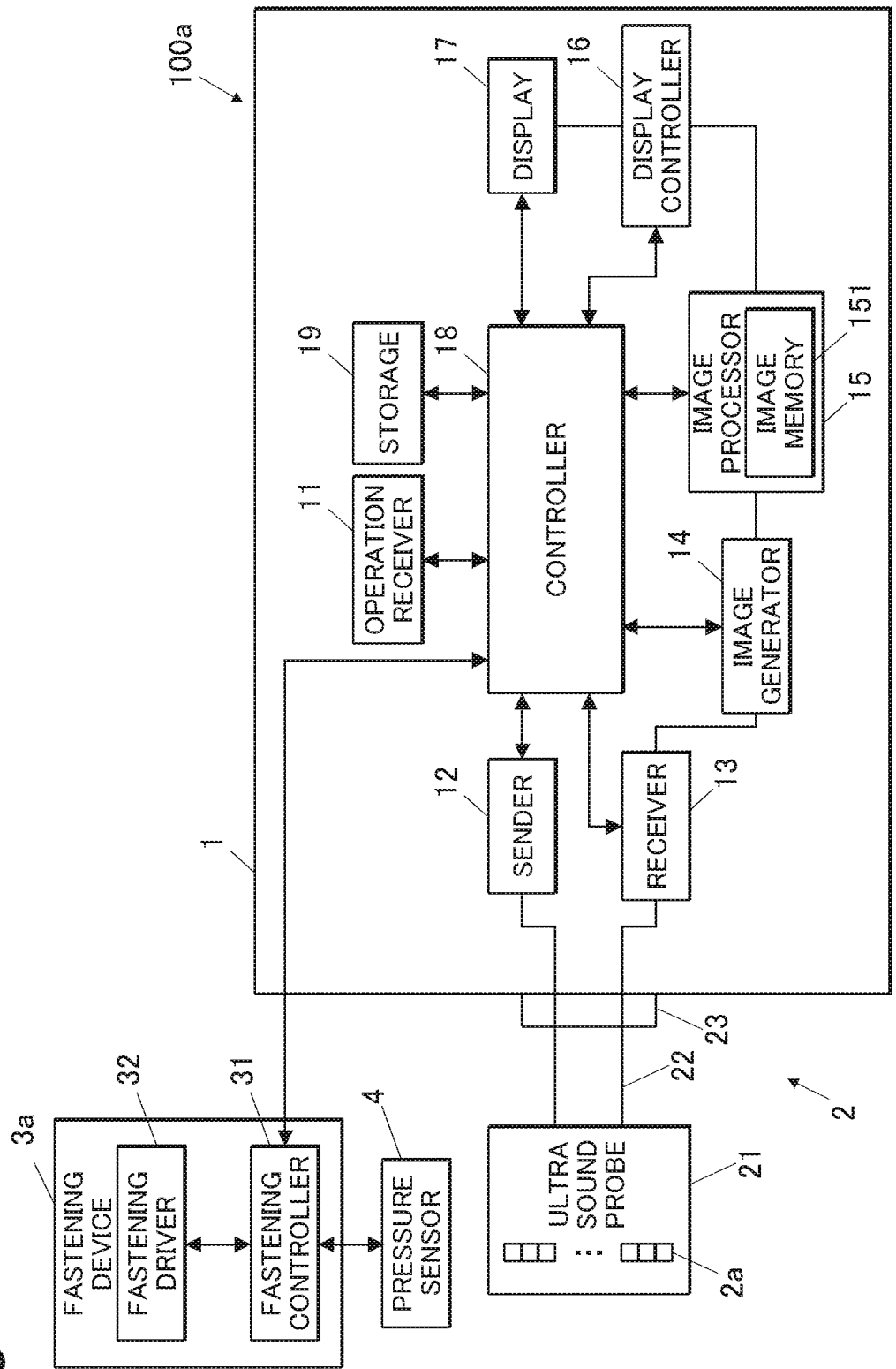
FIG. 8 is a block diagram showing functional components of the ultrasound diagnostic apparatus in a second embodiment.
Figure 9:
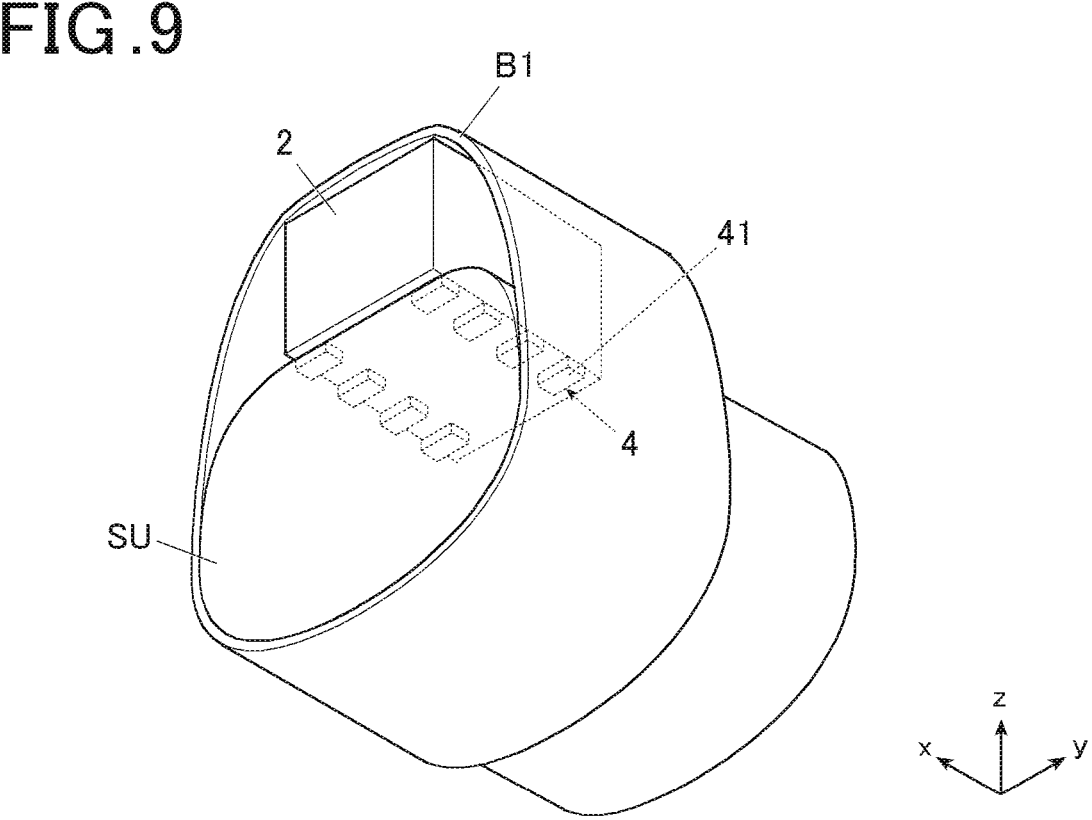
FIG. 9 is a schematic perspective view of the ultrasound probe, a pressure sensor, a band, and the subject in the second embodiment.
Figure 10:
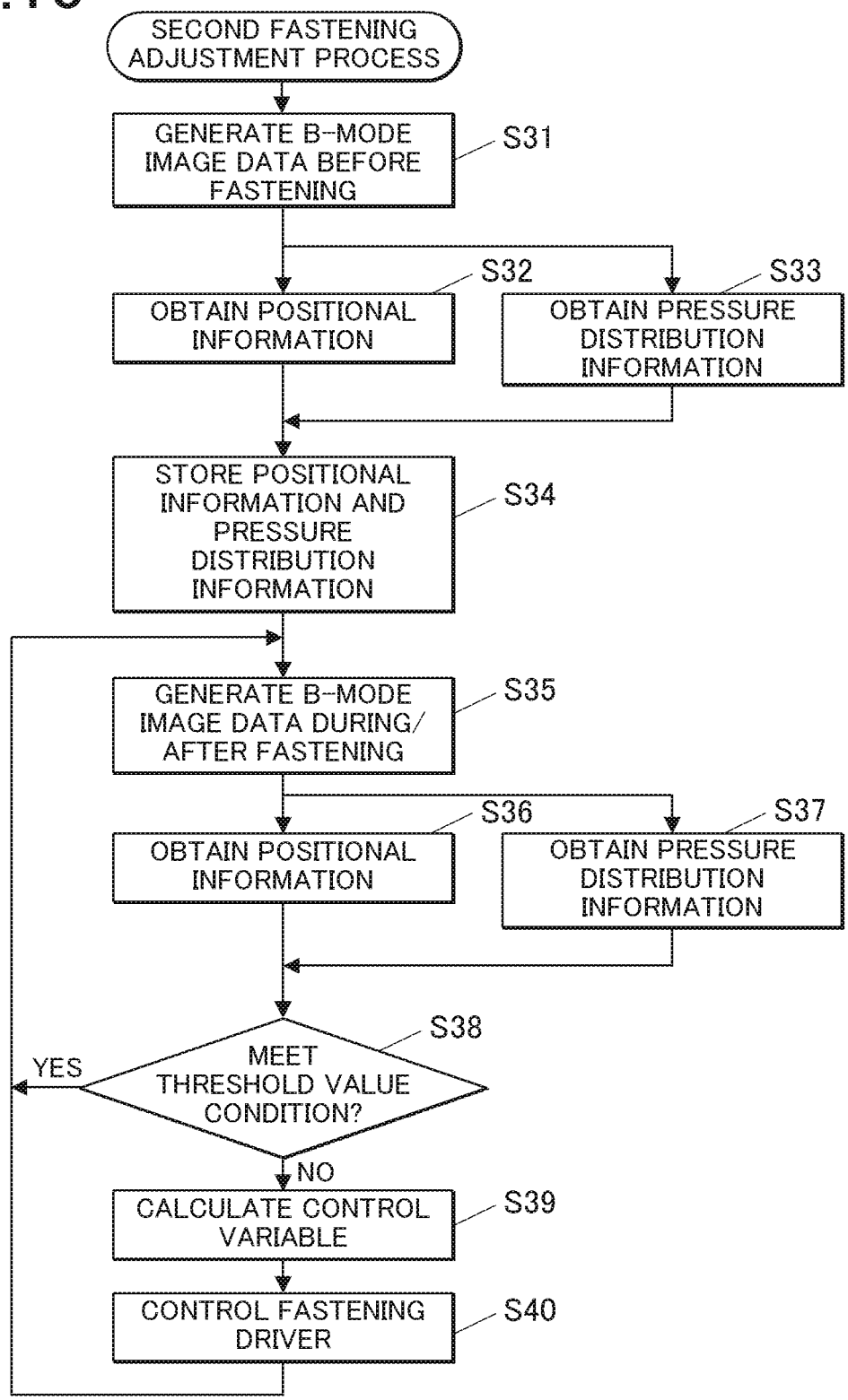
FIG. 10 is a flowchart of a second fastening adjustment process.

The second embodiment of the present invention is described with reference to FIG. 8 to FIG. 10. FIG. 8 is a block diagram showing functional components of an ultrasound diagnostic apparatus 100a in the second embodiment. FIG. 9 is a schematic perspective view of the ultrasound probe 2, a pressure sensor 4, a band B1, and the subject SU in the second embodiment. FIG. 10 is a flowchart of a second fastening adjustment process.

In the above-described first embodiment, the controller 18 calculates the pressure distribution information on the subject on the basis of the positional information (thickness) of the coupler C1 in the B-mode image, and fastens the ultrasound probe 2 to the subject with the fastening device 3 on the basis of the calculated pressure distribution information. In the second embodiment, the pressure distribution information on the subject is obtained by a pressure sensor.

In this embodiment, the ultrasound diagnostic apparatus 100a shown in FIG. 8 is used. Elements of the ultrasound diagnostic apparatus 100a that are the same as that of the ultrasound diagnostic apparatus 100 in the first embodiment are denoted by the same reference numerals and not described herein. The aspects different from the first embodiment are described.

The ultrasound diagnostic apparatus 100a includes an ultrasound diagnostic apparatus main body 1, an ultrasound probe 2, and a fastening device 3a, and a pressure sensor 4. The ultrasound diagnostic apparatus main body 1 is the same as that in the first embodiment. However, the ROM of the controller 18 stores the second fastening adjustment program for executing the second fastening adjustment process to be described later, instead of the first fastening adjustment program.

The fastening device 3a includes a fastening controller 31 and a fastening driver 32 as well as a fastening member for fastening the ultrasound probe 2 to the subject. The pressure sensor 4 includes multiple pressure sensor elements 41 (FIG. 9) that use piezoelectric elements, for example. The pressure sensor 4 detects (obtains) received pressure information and output the pressure information to the fastening controller 31.

Next, the method to detect the pressure applied to the subject SU in this embodiment is described with reference to FIG. 9. As FIG. 9 conceptually shows, the operator fastens the ultrasound probe 2 and the pressure sensor 4 to the subject SU by using the band B1 of the fastening device 3a. The pressure applied to the subject SU increases as the band B1 is tightened.

The pressure sensor 4 is disposed between the body surface of the subject SU and the ultrasound sending-receiving surface at the leading end of the ultrasound probe main body 21 of the ultrasound probe 2. In FIG. 9, the scanning direction, or the direction in which the transducers 2a of the ultrasound probe main body 21 are arranged, are the X-axis direction. The pressure sensor elements 41 of the pressure sensor 4 are arranged two-dimensionally in a matrix on a flat surface defined by the scanning direction (X-axis direction) and the elevation direction (Y-axis direction that is orthogonal to the scanning direction). That is, the pressure sensor elements 41 are arranged on the X-Y surface of the ultrasound sending-receiving surface of the ultrasound probe main body 21. The two-dimensionally arranged pressure sensor elements 41 obtain pressures on the subject at multiple positions on the X-Y surface to obtain two-dimensional pressure distribution information.

As a specific example, the fastening device 3a in the second embodiment is different from the fastening device 3A/3B of the first embodiment in FIG. 5A to FIG. 6 in that the fastening device 3a includes the pressure sensor elements 41 of the pressure sensor 4 instead of the coupler C1. However, the fastening device 3a may include both the coupler C1 and the pressure sensor 4.

Next, the operation of the ultrasound diagnostic apparatus 100a is described with reference to FIG. 10. The second fastening adjustment process to be performed by the ultrasound diagnostic apparatus 100a is described. The second fastening adjustment process is performed when the ultrasound probe 2 is fastened to the subject to obtain ultrasound image data. In the second fastening process, the ultrasound probe 2 is automatically fastened to the subject by the fastening device 3a using the pressure sensor 4 such that the pressure distribution on the subject uniformly increases during/after fastening as compared with the pressure distribution before fastening.

Like the first fastening adjustment process, the threshold value condition for difference information between the pressure distribution information before fastening and the pressure distribution information during/after fastening is set beforehand and stored in the storage 19. The threshold value condition for the difference information on the pressure distribution information is that the pressure distribution information during/after fastening is uniformly increased two-dimensionally by a predetermined value (by x Pascal) as compared with the pressure distribution information before fastening. The operator of the ultrasound diagnostic apparatus 100a attaches the ultrasound probe 2 to an appropriate position of the subject (e.g., leg of a patient) by using the fastening device 3a. To allow the operator to check the position of the observation target of the subject, the controller 18 causes the ultrasound probe 2 to send and receive ultrasound waves to generate B-mode image data and displays it on the display 17 in real time by controlling the sender 12, the receiver 13, the image generator 14, the image processor 15, and the display controller 16. The controller 18 keeps the real-time display while performing the second fastening adjustment process.

In response to the operator inputting a command to perform the second fastening adjustment process with the operation receiver 11, the controller 18 of the ultrasound diagnostic apparatus 100a performs the second fastening adjustment process in accordance with the second fastening adjustment program stored in the ROM.

Step S31 is the same as Step S11 of the first fastening adjustment process in FIG. 7. On the basis of the B-mode image of the B-mode image data before fastening generated n Step S31, the controller 18 obtains positional information of the target before fastening (Step S32). In Step S32, the target is manually or automatically extracted as in Step S12.

The controller 18 obtains the pressure distribution information before fastening from the pressure sensor 4 via the fastening controller 31 (Step S33). The pressure distribution information before fastening indicates the distribution of pressures in the scanning direction and in the elevation direction detected by the pressure sensor elements 41 of the pressure sensor 4. Steps S34, S35 are the same as Steps S14, S15 in FIG. 7.

On the basis of the B-mode image of the B-mode image data during/after fastening generated in Step S35, the controller 18 obtains positional information of the target (Step S36). The controller 18 obtains two-dimensional pressure distribution information during/after fastening from the pressure sensor 4 via the fastening controller 31 (Step S37). Steps S38 to S40 are the same as Steps S18 to S20 in FIG. 7.

According to the second embodiment, the ultrasound diagnostic apparatus 100a includes the pressure sensor 4 that detects pressure distribution information on the subject, and the controller 18 obtains the detected pressure distribution information on the subject. Thus, the second embodiment can directly obtain more accurate pressure distribution information on the subject as well as yielding the same advantageous effect with the first embodiment.

In the above description, the ROM is used as a computer-readable medium that stores the programs of the present invention. However, the computer readable medium is not limited to the ROM. As other computer-readable storage media, a nonvolatile memory, such as a flash memory, and a portable storage medium, such as a CD-ROM, can also be used. Further, a carrier wave may be used as a medium to provide data of the programs of the present invention via a communication line.

The embodiments described above are preferred examples of the ultrasound diagnostic apparatus and the storage medium according to the present invention and does not limit the present invention.

For example, in the first embodiment, the transducers 2a of the ultrasound probe main body 21 of the ultrasound probe 2 are arranged one-dimensionally; B-mode image data is generated as a single ultrasound image; and the pressure application part of the fastening driver 32 of the fastening device 3 is positioned two-dimensionally on the body surface of the subject (e.g., (i) four corners of the cover 33 of the fastening device 3A where the cover 33 is in contact with the wires 351, 352 and (ii) four corners of the base 36 of the fastening device 3B). However, the present invention is not limited to this configuration. For example, the first embodiment may be modified into modifications 1-1 to 1-3 as shown in the following TABLE I.

TABLE I

| | TRANSDUCER ARRANGEMENT | PRESSURE APPLIED PART |
|---|---|---|
| FIRST EMBODIMENT | ONE-DIMENSIONAL | TWO-DIMENSIONAL |
| MODIFICATION 1-1 | TWO-DIMENSIONAL | TWO-DIMENSIONAL |
| MODIFICATION 1-2 | ONE-DIMENSIONAL | ONE-DIMENSIONAL |
| MODIFICATION 1-3 | TWO-DIMENSIONAL | ONE-DIMENSIONAL |

In the modifications 1-1 and 1-3, the transducers 2a of the ultrasound probe main body 21 of the ultrasound probe 2 are arranged two-dimensionally in a matrix. In the modifications 1-1 and 1-3, multiple pieces of three-dimensional B-mode image data are generated in Steps S11 and S15 of the first fastening adjustment process shown in FIG. 7. On the basis of the multiple pieces of B-mode image data, in Steps S13, S17 of the first fastening adjustment process, the controller 18 calculates the pressure distribution information indicating the pressures on the subject at respective two-dimensional positions on the body surface of the subject.

In the modifications 1-2 and 1-3, the pressure-applied region is one-dimensional. In the modifications 1-2 and 1-3, the pressure-applied region to which the pressure is applied by the fastening driver 32 of the fastening device 3 is one-dimensional on the body surface of the subject (e.g., in the scanning direction (X-axis direction) or the elevation direction (Y-axis direction) in FIG. 4).

In the above-described second embodiment, the pressure sensor elements 41 of the pressure sensor 4 are two-dimensionally arranged (in the elevation direction (Y-axis direction) and in the scanning direction (X-axis direction) on the ultrasound sending-receiving surface of the ultrasound probe main body 21 of the ultrasound probe 2 in FIG. 9), and the pressure-applied region to which the pressure is applied by the fastening driver 32 of the fastening device 3 is two-dimensional on the body surface of the subject. However, the present invention is not limited to this. For example, the second embodiment may be modified into modifications 2-1 to 2-3 as shown in the following TABLE II.

TABLE II

| | PRESSURE SENSOR ARRANGEMENT | PRESSURE APPLIED PART |
|---|---|---|
| SECOND EMBODIMENT | TWO-DIMENSIONAL | TWO-DIMENSIONAL |
| MODIFICATION 2-1 | TWO-DIMENSIONAL | ONE-DIMENSIONAL |
| MODIFICATION 2-2 | ONE-DIMENSIONAL | ONE-DIMENSIONAL |
| MODIFICATION 2-3 | ONE-DIMENSIONAL | TWO-DIMENSIONAL |

In the modifications 2-2 and 2-3, the pressure sensor elements 41 of the pressure sensor 4 are arranged one-dimensionally in the ultrasound probe main body 21 in a predetermined direction (e.g., in the scanning direction (X-axis direction) or the elevation direction (Y-axis direction) of the ultrasound probe main body 21). In Steps S33 and S37 of the second fastening adjustment process shown in FIG. 10, the controller 18 calculates one-dimensional pressure distribution information indicating pressures at one-dimensional respective positions on the body surface of the subject, by using the one-dimensionally arranged pressure sensor elements 41.

Figure 11:
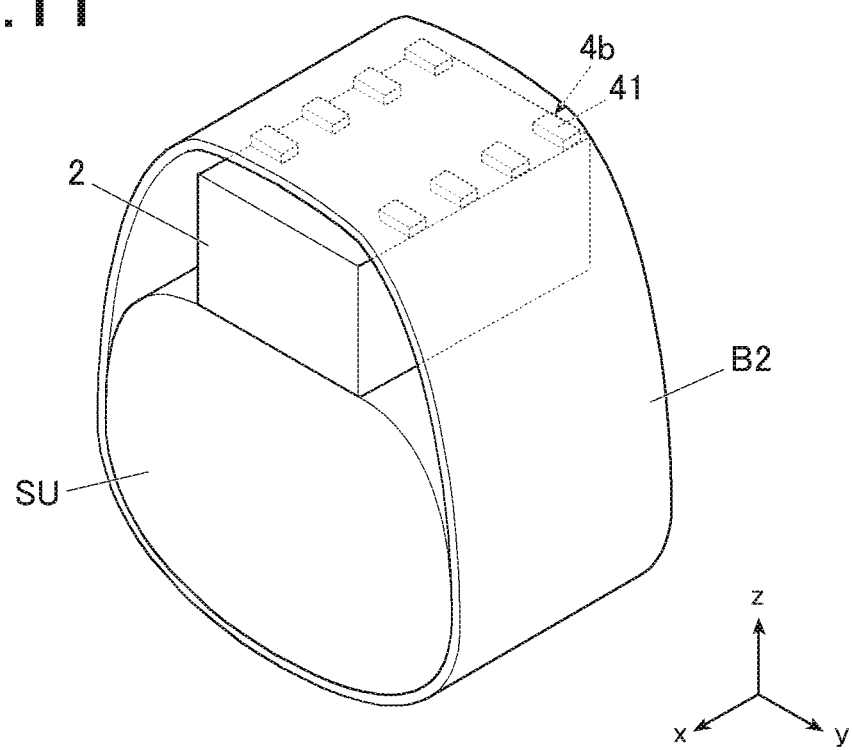
FIG. 11 is a schematic perspective view of an ultrasound probe, a pressure sensor, a band, and a subject in a modification.

Further, in the second embodiment, the pressure sensor 4 is disposed between the subject SU and the front side (−Z direction side, ultrasound sending-receiving surface) of the ultrasound probe main body 21 of the ultrasound probe 2. However, the present invention is not limited to this configuration. For example, in the second embodiment, the pressure sensor 4 may be disposed between the band B2 of the fastening device and the rear side of the ultrasound probe main body 21 of the ultrasound probe 2 (+Z direction side, namely the surface opposite the ultrasound sending-receiving surface), as shown in FIG. 11. FIG. 11 is a schematic perspective view of the ultrasound probe 2, the pressure sensor 4b, the band B2, and the subject SU in the modification. The band B2 of the fastening device is wound around the subject SU, so that the ultrasound probe 2 and the pressure sensor 4b on the ultrasound probe 2 is attached to the subject SU. Like the pressure sensor 4, the pressure sensor 4b includes multiple pressure sensor elements 41 that are arranged two-dimensionally in a matrix on the X-Y flat surface of the ultrasound sending-receiving surface of the ultrasound probe main body 21 (flat surface defined by the scanning direction (X-axis direction) and the elevation direction (Y-axis direction)).

In the modifications 2-2, 2-3 and the modification shown in FIG. 11, in a case where the pressure sensor elements 41 of the pressure sensor 4b are arranged in an one-dimensional direction, it is preferable that the pressure sensor elements 41 be one-dimensionally arranged in the elevation direction (Y-axis direction) orthogonal to the direction in which the transducers 2a of the ultrasound probe main body 21 are arranged (scanning direction, X-axis direction). However, the direction in which the pressure sensor elements 41 are one-dimensionally arranged may be different from the elevation direction.

In the first embodiment, the controller 18 calculates pressure distribution information on the basis of positional information (thickness) of the coupler C1 in the B-mode image, and calculates the control variable of the fastening driver 32 of the fastening device 3 on the basis of changes in the pressure distribution information (difference information between the pressure distribution information before fastening and the pressure distribution information during/after fastening). In the second embodiment, the pressure sensor 4 obtains pressure distribution information, and the controller 18 calculates the control variable of the fastening driver 32 of the fastening device 3a on the basis of changes in the pressure distribution information (difference information). However, the present invention is not limited to this configuration.

For example, the control variable for the fastening driver 32 of the fastening device 3 may be calculated on the basis of changes (difference information) in positional information of the target with respect to the body surface of the subject in the B-mode image. For another example, the control variable for the fastening driver 32 of the fastening device 3 may be calculated on the basis of changes (difference information) in angle information that indicates the angle of the target with respect to the body surface of the subject in the B-mode image. When the positional information/angle information of the target is used to calculate the control variable for the fastening driver 32, the threshold value condition for Step S18 in the first fastening adjustment process in FIG. 7 is that the difference information between positional information/angle information of the target before fastening and positional information/angle information during/after fastening is equal to or less than a predetermined value, for example.

More specifically, when the positional information/angle information of the target is used for controlling the fastening, the positional information/angle information of the target before fastening is obtained in Step S32 of the second fastening adjustment process shown in FIG. 10. Steps S33, S37 are omitted. In Step S34, the positional information/angle information obtained in Step S32 is stored. In Step S36, the positional information/angle information of the target during/after fastening is obtained. In Step S38, it is determined whether or not the difference information between the positional information/angle information before fastening obtained in Step S32 and the positional information/angle information during/after fastening obtained in Step S36 meets the threshold value condition. The threshold value condition may be that the difference information (error) indicating the amount of movement of the target before and after the subject SU moves is equal to or less than a predetermined value, when a pressure is applied to the subject SU (the subject SU is tightened by the band) under the control of the fastening device 3 and then the subject SU moves.

Thus, the control variable for the fastening driver 32 of the fastening device 3/3a may be calculated on the basis of changes (difference information) in at least one of the following: positional information of the target with respect to the body surface of the subject in the B-mode image; angle information of the target with respect to the body surface of the subject in the B-mode image; positional information (thickness information) of the coupler C1 in the B-mode image; and pressure distribution information on the subject detected by the pressure sensor 4. According to such a configuration, the ultrasound probe 2 can be fastened to the subject appropriately, automatically, and easily, without causing positional deviation of the ultrasound probe 2 on the body surface of the subject and pressure unevenness. This reduces burdens on the operator and yields desired ultrasound image data.

The detailed configuration and operation of the components constituting the ultrasound diagnostic apparatus 100/100a in the above embodiments can be appropriately modified without departing from the scope of the present invention.

Although embodiments of the present invention have been described and illustrated in detail, the disclosed embodiments are made for purposes of illustration and example only and not limitation. The scope of the present invention should be interpreted by terms of the appended claims

What is claimed is:
1. An ultrasound diagnostic apparatus comprising:
an image generator that generates ultrasound image data based on a reception signal received from an ultrasound probe, the ultrasound probe sending and receiving ultrasound waves;
a fastener configured to fasten the ultrasound probe to a subject such that a pressure applied to the subject to which the ultrasound probe is fastened is adjustable; and
a hardware processor that controls driving of the fastener, based on difference information between before fastening the ultrasound probe and during/after fastening the ultrasound probe, the difference information being on at least one of positional information on a position of an observation target of the subject, angle information on an angle of the observation target, and pressure information on the pressure applied to the subject,
wherein the fastener comprises a belt-shaped band that is configured to be wound around the subject, a cover that covers the ultrasound probe and that is connected to the band, and a fastening driver to which ends of the band are connected and that, when driven in a state in which the band is wound around the subject and the ultrasound probe is pressed against the subject, is capable of applying a pulling force to the ends of the band to tighten the band to thereby apply a force to the cover, fasten the ultrasound probe to the subject and apply the pressure to the subject, the fastener further comprises wires, wherein first ends of the wires are connected to the fastening driver and second ends of the wires are respectively connected to the ends of the band, wherein the fastening driver is configured to individually and independently wind up and send out each wire to adjust a pressure applied at respective positions where each wire contacts the cover.

2. The ultrasound diagnostic apparatus according to claim 1, wherein the hardware processor obtains the positional information or the angle information of the target, based on an image of the target in an ultrasound image of the generated ultrasound image data.

3. The ultrasound diagnostic apparatus according to claim 1, wherein
the fastener is configured to be disposed between the ultrasound probe and the subject and includes an elastic body having a predetermined elastic modulus, and
the hardware processor calculates the pressure information on the pressure applied to the subject, based on an image of the elastic body in an ultrasound image of the generated ultrasound image data.

4. The ultrasound diagnostic apparatus according to claim 1, further comprising a pressure sensor that detects the pressure information on the pressure applied to the subject, wherein the hardware processor obtains the detected pressure information.

5. The ultrasound diagnostic apparatus according to claim 1, wherein
the hardware processor determines whether or not the difference information between before fastening the ultrasound probe and during/after fastening the ultrasound probe meets a threshold value condition, the threshold value condition concerning controlling the fastener, the difference information being on at least one of the positional information, the angle information, and the pressure information, and
based on the determination, the hardware processor controls driving of the fastener.

6. The ultrasound diagnostic apparatus according to claim 5, wherein the threshold value condition corresponds to a part of the subject to which the ultrasound probe is fastened.

7. A non-transitory computer-readable storage medium storing a program for a computer of an ultrasound diagnostic apparatus that includes: an image generator that generates ultrasound image data based on a reception signal received from an ultrasound probe that sends and receives ultrasound waves; and a fastener configured to fasten the ultrasound probe to a subject such that a pressure applied to the subject to which the ultrasound probe is fastened is adjustable, wherein the fastener comprises a belt-shaped band that is configured to be wound around the subject, a cover that covers the ultrasound probe and that is connected to the band, and a fastening driver to which ends of the band are connected and that, when driven in a state in which the band is wound around the subject and the ultrasound probe is pressed against the subject, is capable of applying a pulling force to the ends of the band to tighten the band to thereby apply a force to the cover, fasten the ultrasound probe to the subject and apply the pressure to the subject, wherein the fastener further comprises wires, wherein first ends of the wires are connected to the fastening driver and second ends of the wires are respectively connected to the ends of the band, wherein the fastening driver is configured to individually and independently wind up and send out each wire to adjust a pressure applied at respective positions where each wire contacts the cover,
wherein the program causes the computer of the ultrasound diagnostic apparatus to function as a hardware processor that controls driving of the fastener, based on difference information between before fastening the ultrasound probe and during/after fastening the ultrasound probe, the difference information being on at least one of positional information on a position of an observation target of the subject, angle information on an angle of the observation target, and pressure information on the pressure applied to the subject.

* * * * *